United States Patent
Kowalczyk

(10) Patent No.: US 7,610,102 B2
(45) Date of Patent: Oct. 27, 2009

(54) STRAIN RELIEF SYSTEM FOR SPINAL CORD STIMULATION LEAD

(76) Inventor: James M. Kowalczyk, 4803 Hepplewhite Dr., Manlius, NY (US) 13104

( * ) Notice: Subject to any disclaimer, the term of this patent is extended or adjusted under 35 U.S.C. 154(b) by 0 days.

(21) Appl. No.: 12/353,529

(22) Filed: Jan. 14, 2009

(65) Prior Publication Data
US 2009/0118807 A1    May 7, 2009

Related U.S. Application Data

(63) Continuation of application No. 11/924,070, filed on Oct. 25, 2007.

(51) Int. Cl.
*A61N 1/05* (2006.01)
(52) U.S. Cl. .............. 607/117; 604/174; 604/175; 607/116
(58) Field of Classification Search .......... 600/30, 600/373, 375, 377, 393, 395; 604/174, 175, 604/177, 180, 535; 607/116–123, 126, 130, 607/149
See application file for complete search history.

(56) References Cited

U.S. PATENT DOCUMENTS

| | | | |
|---|---|---|---|
| 4,516,584 A | 5/1985 | Garcia | |
| 4,537,183 A | 8/1985 | Fogarty | |
| 4,553,961 A | 11/1985 | Pohndorf et al. | |
| 4,650,473 A | 3/1987 | Bartholomew et al. | |
| 5,107,856 A | 4/1992 | Kristiansen et al. | |
| 5,129,405 A | 7/1992 | Milijasevic et al. | |
| 5,152,298 A | 10/1992 | Kreyenhagen et al. | |
| 5,238,007 A | 8/1993 | Giele et al. | |
| 5,273,053 A | 12/1993 | Pohndorf | |
| 5,405,339 A | 4/1995 | Kohnen et al. | |
| 5,423,763 A | 6/1995 | Helland et al. | |
| 5,476,493 A | 12/1995 | Muff | |
| 5,584,874 A | 12/1996 | Rugland et al. | |
| 5,603,730 A | 2/1997 | Romkee | |
| 5,628,780 A | 5/1997 | Helland et al. | |
| 5,637,098 A | 6/1997 | Bierman | |
| 5,733,322 A * | 3/1998 | Starkebaum | 607/117 |
| 5,746,722 A | 5/1998 | Pohndorf et al. | |
| 5,843,146 A | 12/1998 | Cross, Jr. | |
| 6,377,853 B1 | 4/2002 | Malaney et al. | |
| 6,473,654 B1 | 10/2002 | Chinn | |
| 6,668,198 B2 | 12/2003 | Swanson et al. | |
| 6,985,777 B2 | 1/2006 | Tsuboi et al. | |
| 6,997,919 B2 | 2/2006 | Olsen et al. | |
| 7,149,587 B2 | 12/2006 | Wardle et al. | |

(Continued)

*Primary Examiner*—Carl H Layno
*Assistant Examiner*—Jennifer Stewart
(74) *Attorney, Agent, or Firm*—George R. McGuire; David L. Nocilly; Bond Schoeneck & King, PLLC

(57) ABSTRACT

An anchor for spinal electrical stimulation leads having a first, extended portion adapted to be inserted through the spine and into the spinal column, and a second, shorter portion adapted to be sutured to the fascia on the outside of the spine. The extended portion assists with positioning of the electrode tip onto the spinal cord on provides strain relief for the electrode. The anchor further comprises an inner tube disposed inside of the housing along an intermediate portion between the extended portion and the shorted portion. When the outside portion of the tubular housing is sutured to the fascia of a patient, the inner tube is compressed against the electrical lead, thereby locking it in place and preventing migration over time.

8 Claims, 3 Drawing Sheets

U.S. PATENT DOCUMENTS

| | | |
|---|---|---|
| 2002/0077687 A1 | 6/2002 | Ahn |
| 2002/0165589 A1 | 11/2002 | Imran et al. |
| 2003/0078642 A1 | 4/2003 | Malaney et al. |
| 2003/0167025 A1 | 9/2003 | Imran et al. |
| 2004/0116992 A1 | 6/2004 | Wardle et al. |
| 2005/0288722 A1 | 12/2005 | Eigler et al. |
| 2007/0078399 A1* | 4/2007 | Olson ......................... 604/175 |
| 2008/0275401 A1* | 11/2008 | Sage et al. .................. 604/175 |

* cited by examiner

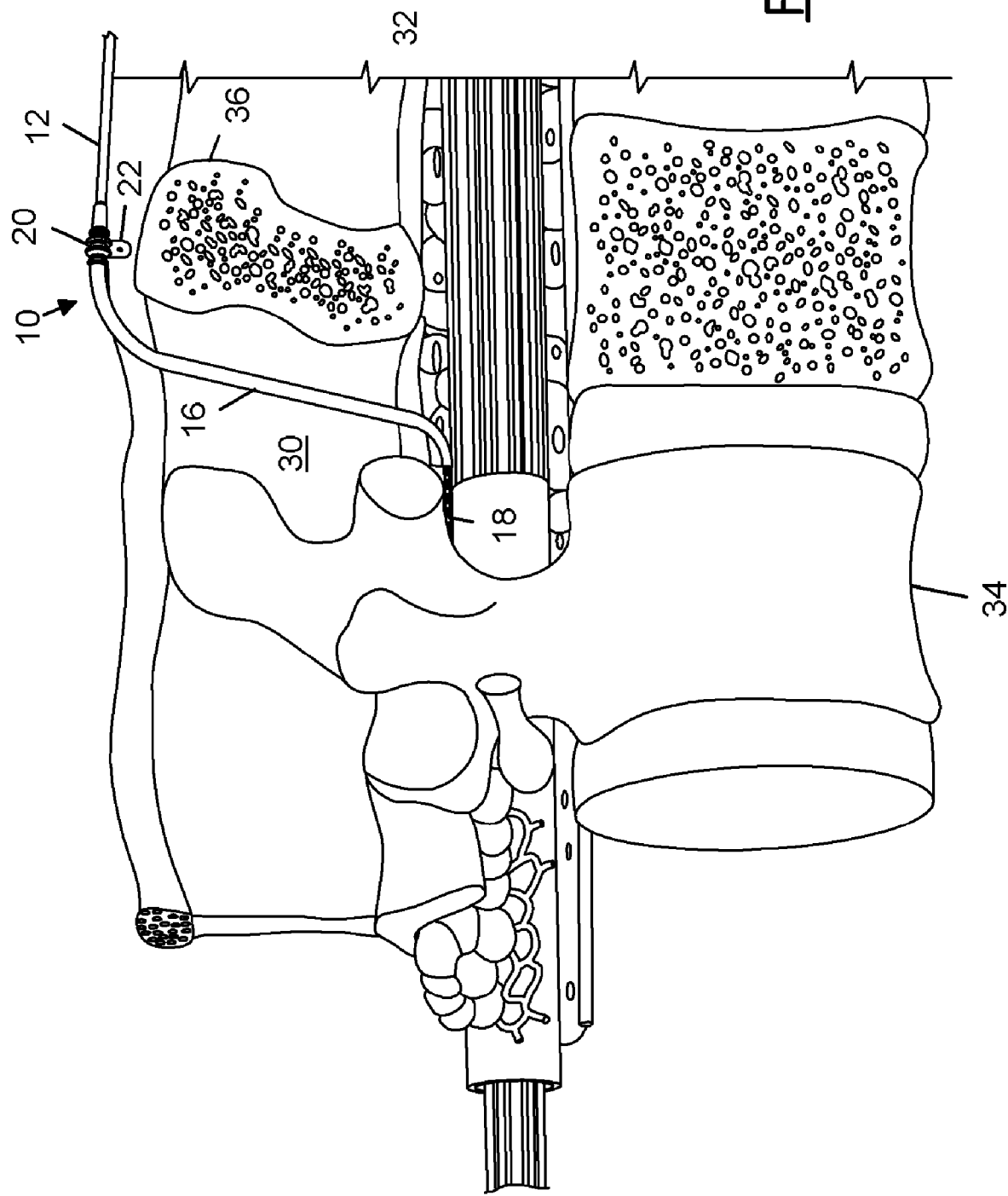

STRAIN RELIEF SYSTEM FOR SPINAL CORD STIMULATION LEAD

RELATED APPLICATION

The present application is a continuation of U.S. application Ser. No. 11/924,070, filed on Oct. 25, 2007; all of the foregoing patent-related document(s) are hereby incorporated by reference herein in their respective entirety(ies).

BACKGROUND OF THE INVENTION

1. Field of the Invention

The present invention relates to medical devices and, more particularly, to a strain relief system for implantable electrical stimulation leads.

2. Description of the Related Art

Spinal cord stimulation (SCS) is frequently used to treat patients with chronic neuropathic pain who have not found relief using other treatments. In general, neurostimulation works by applying an electrical current to the nerves located near the source of chronic pain. More particularly, a thin wire with an electrical lead at one end is implanted into a patient in the location to be treated, such as a particular portion of the spine. An electrical generator connected to the wire is used to deliver electrical current to the lead, thereby stimulating the nerves at the treatment location.

Although spinal cord stimulation may produce dramatic results for patient pain care, the systems used to supply the electrical stimulation to the spine are subject to failure and may lead to reduced effectiveness or require additional surgery to correct or replace the defective portions of the system. The most common complications associated with spinal cord stimulation fall into two general categories. The first category of problems that affects spinal cord stimulation systems is the migration of the electrodes away from the intended targets. This complication may occur in over ten percent of patients receiving spinal cord stimulation. The second category of problems that affects spinal cord stimulation systems is the breakage of the electrical leads. This complication may occur in nearly ten percent of patients receiving spinal cord stimulation. As a result of these complications, the spinal cord stimulation system may need to be repaired or replaced, if possible, through additional patient surgical procedures. Thus, the risks to the patient of more serious complications and the overall costs associated with obtaining neurostimulation treatment are increased.

Convention methods for affixing stimulation leads in place include suture sleeves having elastomeric gripping portions positioned therein. When the suture sleeve is sutured into position along the spinal column, the gripping sleeve is compressed around the pacing lead, thereby enhancing retention of the lead. While such systems may limit lead migration, they do not limit the stresses that cause fracturing or breaking of the lead wires. Conventional methods for reducing fracturing involve the use of strain relief members that extend from the lead anchors. Unfortunately, these strain relief members simply relocate stress points and thus fail to reduce the occurrence of fractures.

BRIEF SUMMARY OF THE INVENTION

It is therefore a principal object and advantage of the present invention to provide a system and method for anchoring spinal cord stimulation leads that reduces lead migration.

It is a further object and advantage of the present invention to provide a system and method for anchoring spinal cord stimulation leads that reduces lead fractures.

It is an additional object and advantage of the present invention to provide a system for anchoring spinal cord stimulation leads that reduces the risks to patients.

It is another object and advantage of the present invention to provide a system for anchoring spinal cord stimulation leads that reduces the risks to patients.

In accordance with the foregoing objects and advantages, the present invention is an anchor for spinal electrical stimulation leads. The anchor comprises a flexible, tubular housing through which an electrical stimulation electrode may be passed. The housing generally comprises a central portion adapted for attachment to the fascia of the spine, a rear portion extending from the back of the central portions, and a front portion extending forwardly from the central portion. The central portion of the housing may optionally comprise a pair of flanges extending transversely outwardly, each of which includes a pair of holes formed therethrough for accepting the sutures. The central portion of the housing may further include an inner tube disposed therein. When the central portion of the tubular housing is sutured to the fascia of a patient, the inner tube is compressed against the electrical lead, thereby locking it in place and preventing migration of the lead. The front portion of the housing is dimensioned to be inserted at least partially through the ligamentum flavum (interspinal ligament) and, preferably, entirely through the ligamentum flavum into the epidural space of the spine. The anchor is preferably manufactured from a flexible polymer so that the front portion of the housing can bend flex after passing through the spine and into the spinal cavity, thereby providing strain relief for an electrical lead passing therethough and reducing fracturing of the electrical lead. The material used to form the anchor may further be impregnated with barium so that the anchor is visible when imaged using a fluoroscope.

BRIEF DESCRIPTION OF THE DRAWINGS

The present invention will be more fully understood and appreciated by reading the following Detailed Description in conjunction with the accompanying drawings, in which:

FIG. 5 is a partial cross-sectional view of spinal column including an embodiment of an electrical stimulation lead anchor according to the present invention.

DETAILED DESCRIPTION OF THE INVENTION

Figure 1:
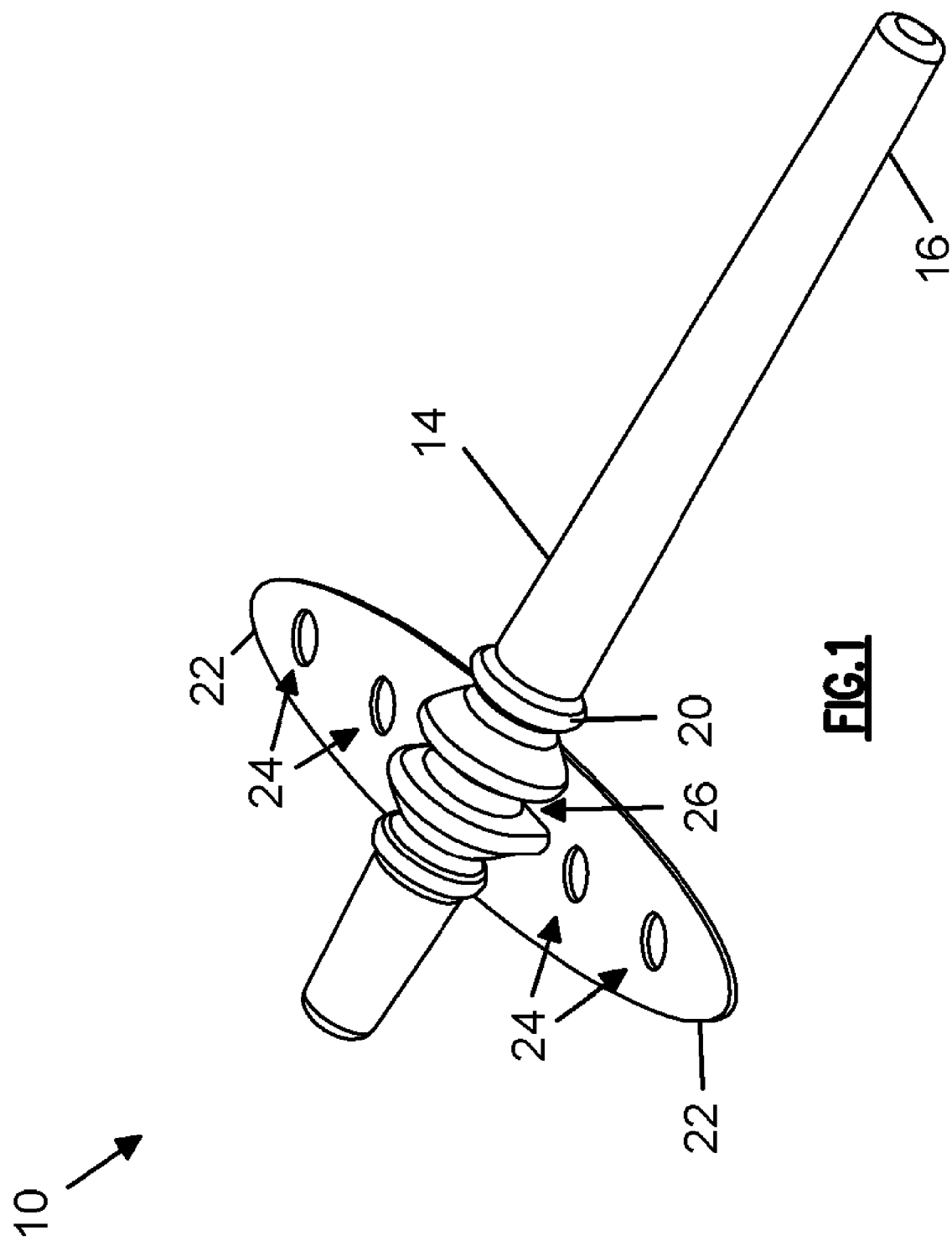
FIG. 1 is perspective view of an electrical stimulation lead anchor according to the present invention.

Referring now to the drawings, wherein like reference numerals refer to like parts throughout, there is seen in FIG. 1 an anchor 10 for providing strain relief to a spinal electrical stimulation lead 12 passing therethrough. Anchor 10 comprising a flexible, tubular housing 14 through which electrical stimulation lead 12 passes. Housing 14 includes a front portion 16 adapted to be inserted at least partially through the ligamentum flavum and, preferably, entirely through the ligamentum flavum into the epidural space of the spinal column to assist in positioning the electrode tip 18 of lead 12 onto the appropriate portions of the spinal cord.

Housing 14 includes a central portion 20 adapted to be sutured to the fascia on the outside of the spine. Central portion 20 of housing 14 may further optionally comprise a set of flanges 22 extending from opposing sides of housing 14 to provide additional locations for the attachment of sutures. Each flange 22 includes a pair of apertures 24 formed therethrough. Apertures 24 are dimensioned to accept the sutures used to secure anchor 10 to the fascia of the spine. Central portion 20 of housing 14 may also include a series of grooves 26 formed in an outer portion thereof to provide for interlocking of anchor 10 with the sutures used to secure anchor 10 to the fascia of the spine.

Figure 4:
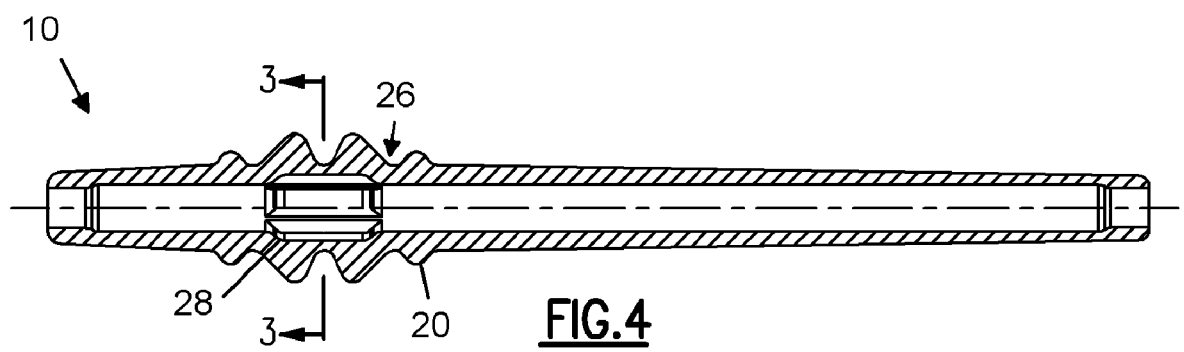
FIG. 4 is a longitudinal cross-section of an electrical stimulation lead anchor according to the present invention.
Figure 2:
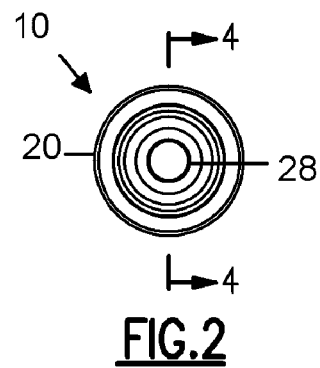
FIG. 2 is a front end view of another embodiment of an electrical stimulation lead anchor according to the present invention.
Figure 3:
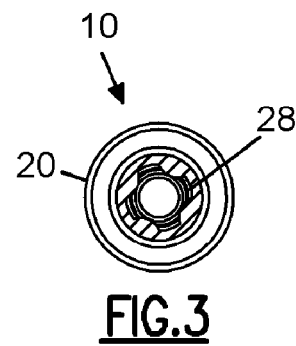
FIG. 3 is a rear end view of an electrical stimulation lead anchor according to the present invention.

Referring to FIGS. 2 through 4, central portion 20 may include a tube 28 positioned therein for assisting in clamping against lead 12 when anchor 10 is sutured to the fascia of the spine. When outside portion of housing 14 is sutured to the fascia of a patient, inner tube 28 is compressed against electrical lead 12, thereby locking lead 12 in place and preventing migration of lead 12 after insertion into a patient. Anchor 10 is preferable manufactured from a flexible polymer so that extended portion 16 of housing 14 can flex after passing through the spine and into the spinal cavity, thereby providing strain relief for electrical lead 12 passing therethough, thereby reducing fracturing of electrical lead 12 when in use by a patient. Preferably, anchor 10 is manufactured from a polymer having a durometer of between about 40 and about 60 to provide sufficient flexibility for insertion of extended portion 16 of housing 14 into or through the ligamentum flavum and providing strain relief for a lead passing therethough. It should be recognized that those of ordinary skill in the art in that anchor 10 should be manufactured to be slightly less or more pliable than lead 12 to provide strain relief and reduce failures, depending on the particular lead 12 being used with anchor 10. Anchor 10 may further be impregnated with barium so that anchor 10 is visible on x-rays.

Referring to FIG. 5, front portion 16 is dimensioned to be inserted at least partially through the ligamentum flavum 30 and, as preferably shown, entirely through the ligamentum flavum 30 into the epidural space 32 of spinal column 34. The particular angle of insertion of front portion 16 is not shown to scale in FIG. 5, and is preferably greater than ninety degrees with respect to the longitudinal axis of spinal column 34. Those of skill in the art will recognize that the particular dimensions of front portion 16 and angle of insertion into ligamentum flavum 30 will vary according to the anatomy of the particular patient. Generally, in order for front portion 16 of anchor 10 to reach into ligamentum flavum 30 from the anchor point atop the spinus process 36, front portion 16 will need to be between about 12 and about 18 centimeters long. It should be recognized by those of skill in the art that the length of front portion 16 depends on the physical structure of the patient and may be determined with relation to the size of the patient. Anchor 10 may thus be manufactured in various lengths to be selected by the surgeon after determining the appropriate length front portion 16 for the particular patient, or front portion 16 of anchor 10 may be configured to be trimmed by the surgeon to the appropriate length.

What is claimed is:

1. An apparatus for anchoring a neurostimulation lead in a patient, comprising: a tubular housing having a first portion for anchoring the housing proximately to the spin us process of the patient and a second portion extending from the first portion for providing strain relief; at least one groove extending circumferentially around the first portion of the housing; a tube positioned in the first portion of the housing in operative association with said at least one groove; and wherein said second portion is configured to extend entirely through the ligamentum flavum into the epidural space of the patient when said first portion is attached to the patient.

2. The apparatus of claim 1, wherein the second portion is longer than said first portion.

3. The apparatus of claim 1, wherein the tube is compressible.

4. The apparatus of claim 1, wherein the housing has a durometer between about forty and sixty.

5. The apparatus of claim 1, wherein said apparatus is at least partially radiopaque.

6. The apparatus of claim 5, wherein said apparatus is at least partially impregnated with barium.

7. The apparatus of claim 1, wherein said apparatus is entirely radiopaque.

8. The apparatus of claim 7, wherein said apparatus is completely impregnated with barium.

* * * * *

UNITED STATES PATENT AND TRADEMARK OFFICE
CERTIFICATE OF CORRECTION

PATENT NO. : 7,610,102 B2  Page 1 of 1
APPLICATION NO. : 12/353529
DATED : October 27, 2009
INVENTOR(S) : James M. Kowalczyk It is certified that error appears in the above-identified patent and that said Letters Patent is hereby corrected as shown below:

Column 4, Claim 1, line 19 the words "spin us" should read --spinus--

Signed and Sealed this

Nineteenth Day of January, 2010

David J. Kappos
*Director of the United States Patent and Trademark Office*